US010081616B2

(12) United States Patent
Zhang et al.

(10) Patent No.: US 10,081,616 B2
(45) Date of Patent: Sep. 25, 2018

(54) SOLUBLE EPOXIDE HYDROLASE INHIBITORS AND USES THEREOF

(71) Applicant: X-Chem, Inc., Waltham, MA (US)

(72) Inventors: Ying Zhang, Lexington, MA (US); Anthony D. Keefe, Cambridge, MA (US); Christoph Dumelin, Zurich (CH)

( * ) Notice: Subject to any disclaimer, the term of this patent is extended or adjusted under 35 U.S.C. 154(b) by 0 days.

(21) Appl. No.: 15/504,223

(22) PCT Filed: Aug. 26, 2015

(86) PCT No.: PCT/US2015/046878
§ 371 (c)(1),
(2) Date: Feb. 15, 2017

(87) PCT Pub. No.: WO2016/033150
PCT Pub. Date: Mar. 3, 2016

(65) Prior Publication Data
US 2017/0240526 A1 Aug. 24, 2017

Related U.S. Application Data

(60) Provisional application No. 62/043,275, filed on Aug. 28, 2014.

(51) Int. Cl.
*C07D 401/12* (2006.01)
*C07D 213/81* (2006.01)
*A61K 31/4412* (2006.01)
*A61P 35/00* (2006.01)

(52) U.S. Cl.
CPC ........ *C07D 401/12* (2013.01); *A61K 31/4412* (2013.01); *C07D 213/81* (2013.01)

(58) Field of Classification Search
CPC .... C07D 213/81; C07D 401/12; A61K 31/44; A61K 31/4439
USPC .......................... 546/314, 316, 563; 514/355
See application file for complete search history.

(56) References Cited

FOREIGN PATENT DOCUMENTS

| CN | 104016914 A | 9/2014 |
|---|---|---|
| DE | 3245950 A1 | 7/1983 |
| EP | 2149551 A1 | 2/2010 |
| EP | 2149552 A1 | 2/2010 |
| WO | WO-2007/106705 A1 | 9/2007 |
| WO | WO-2008/152099 A2 | 12/2008 |
| WO | WO-2009/151800 A1 | 12/2009 |
| WO | WO-2010/080183 A1 | 7/2010 |
| WO | WO-2013/112751 A1 | 8/2013 |

OTHER PUBLICATIONS

DE 3245950 A1, Jul. 7, 1983; Machine Translation.*
CN 104016914 A, Sep. 3, 2014.*
International Search Report and Written Opinion for International Patent Application No. PCT/US2015/046878, dated Jan. 20, 2016 (11 pages).
Invitation to Pay Additional Fees for International Application No. PCT/US2015/046878, dated Nov. 2, 2015 (3 pages).
PubChem SID 144204494, dated Oct. 6, 2012, retrieved Oct. 1, 2012 (8 pages).
PubChem. SID 201507607, dated Nov. 11, 2015 (5 pages).
International Preliminary Report on Patentability for International Patent Application No. PCT/US2015/046878, dated Feb. 28, 2017 (6 pages).
Litovchick et al., "Encoded Library Synthesis Using Chemical Ligation and the Discovery of sEH Inhibitors from a 334-Million Member Library," Sci Rep. 5:10916 (2015).
Extended European Search Report for European Application No. 15837061.9, dated Mar. 20, 2018 (7 pages).

* cited by examiner

*Primary Examiner* — Venkataraman Balasubramanian
(74) *Attorney, Agent, or Firm* — Clark & Elbing LLP

(57) ABSTRACT

The present invention features compounds having soluble epoxide hydrolase inhibitory activity. The compounds of the invention, alone or in combination with other pharmaceutically active agents, can be used for treating or preventing various medical conditions, such as cardiovascular diseases, respiratory diseases, inflammation, and diabetes.

14 Claims, No Drawings

SOLUBLE EPOXIDE HYDROLASE INHIBITORS AND USES THEREOF

BACKGROUND OF THE INVENTION

Soluble epoxide hydrolase (sEH) is an enzyme involved in the conversion of epoxyeicosatrienoic acids (EETs) to dihydroxyeicosatrienoic acids (DHETs). Various studies have shown that EETs have anti-inflammatory properties, and so it has been suggested that inhibitors of sEH could have beneficial effects in COPD, cardiovascular disease, and even diabetes. Thus, there is a need for new compounds that inhibit sEH and treatment methods using such compounds.

SUMMARY OF THE INVENTION

The invention features a compound having the formula:

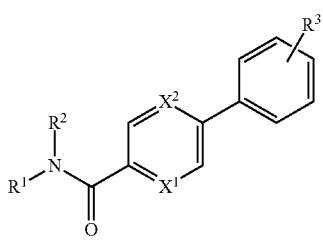

Formula I wherein one of $X^1$ or $X^2$ is N and the other is CH;

$R^1$ is hydrogen, $C_1$-$C_6$ acyl, $C_1$-$C_6$ alkyl, $C_2$-$C_6$ alkenyl, $C_2$-$C_6$ alkynyl, $C_1$-$C_6$ heteroalkyl, $C_2$-$C_6$ heteroalkenyl, $C_2$-$C_6$ heteroalkynyl, $C_3$-$C_{10}$ carbocyclyl, $C_6$-$C_{10}$ aryl, $C_6$-$C_{10}$ aryl $C_1$-$C_6$ alkyl, $C_2$-$C_9$ heterocyclyl, $C_2$-$C_9$ heterocyclyl $C_1$-$C_6$ alkyl;

$R^2$ is hydrogen or $C_1$-$C_6$ alkyl;

$R^3$ is hydrogen, hydroxyl, halogen, thiol, $C_1$-$C_6$ acyl, $C_1$-$C_6$ alkyl, $C_2$-$C_6$ alkenyl, $C_2$-$C_6$ alkynyl, $C_1$-$C_6$ heteroalkyl, $C_2$-$C_6$ heteroalkenyl, $C_2$-$C_6$ heteroalkynyl, $C_3$-$C_{10}$ carbocyclyl, $C_6$-$C_{10}$ aryl, $C_6$-$C_{10}$ aryl $C_1$-$C_6$ alkyl, $C_2$-$C_9$ heterocyclyl, $C_2$-$C_9$ heterocyclyl $C_1$-$C_6$ alkyl, —C(O)NHR$^4$; and $R^4$ is hydrogen, $C_1$-$C_6$ acyl, $C_1$-$C_6$ alkyl, $C_2$-$C_6$ alkenyl, $C_2$-$C_6$ alkynyl, $C_1$-$C_6$ heteroalkyl, $C_2$-$C_6$ heteroalkenyl, $C_2$-$C_6$ heteroalkynyl, $C_3$-$C_{10}$ carbocyclyl, $C_6$-$C_{10}$ aryl, $C_6$-$C_{10}$ aryl $C_1$-$C_6$ alkyl, $C_2$-$C_9$ heterocyclyl, $C_2$-$C_9$ heterocyclyl $C_1$-$C_6$ alkyl;

or a pharmaceutically acceptable salt thereof.

In some embodiments, the compound has the structure:

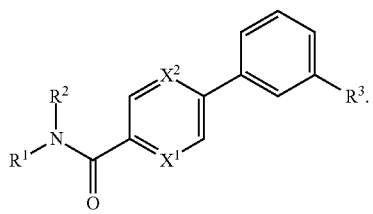

In other embodiments, $R^3$ is —C(O)NHR$^4$. In certain embodiments, $R^4$ is $C_3$-$C_{10}$ carbocyclyl (e.g., cyclohexyl) or $C_6$-$C_{10}$ aryl $C_1$-$C_6$ alkyl (e.g., benzyl). In some embodiments, $R^2$ is $C_1$-$C_6$ alkyl (e.g., methyl). In other embodiments, $X^1$ is N and $X^2$ is CH. In certain embodiments, $X^1$ is CH and $X^2$ is N. In some embodiments, $R^1$ is $C_2$-$C_9$ heterocyclyl $C_1$-$C_6$ alkyl (e.g., pyrazolyl ethyl such as, pyrazo-1-yl ethyl.

In another aspect, the invention features a compound having the structure:

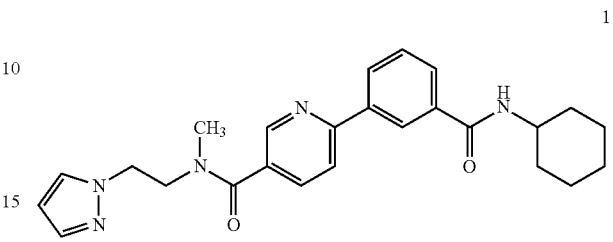

or a pharmaceutically acceptable salt thereof.

In another aspect, the invention features a pharmaceutical composition including any of the foregoing compounds and a pharmaceutically acceptable excipient.

In another aspect, the invention features a method for the treatment of a cardiovascular disease (e.g., hypertension, cardiac hypertrophy, arteriosclerosis, coronary artery calcification, coronary heart disease, ischemia, or reperfusion injury) in a subject in need thereof. This method includes administering to the subject an effective amount of any of the foregoing compounds or pharmaceutical compositions.

In another aspect, the invention features a method for the treatment of cancer in a subject in need thereof. This method includes administering to the subject an effective amount of any of the foregoing compounds or pharmaceutical compositions.

Non-limiting exemplary cancers include leukemia, including acute myeloid leukemia (AML), acute lymphocytic leukemia (ALL), chronic myeloid leukemia (CML), chronic lymphocytic leukemia (CLL), hairy cell leukemia, chronic myelomonocytic leukemia (CMML), juvenile myelomonocytic leukemia (JMML), and B-cell prolymphocytic leukemia (B-PLL); lymphomas, including Hodgkin and non-Hodgkin lymphoma, such as B-cell lymphomas (e.g., diffuse large B-cell lymphoma (e.g., mediastinal (thymic) large B-cell lymphoma and intravascular large B-cell lymphoma), follicular lymphoma, small lymphocytic lymphoma (SLL), chronic lymphocytic leukemia/small lymphocytic lymphoma (CLL/SLL), mantle cell lymphoma (e.g., relapsed or refractory), marginal zone B-cell lymphomas, Burkitt lymphoma, lymphoplasmacytic lymphoma, hairy cell leukemia, primary central nervous system (CNS) lymphoma, primary effusion lymphoma, and lymphomatoid granulomatosis); myelomas, including multiple myeloma, plasmacytoma, localized myeloma, and extramedullary myeloma; and other cancers, such as pancreatic neoplasms, including pancreatic exocrine tumors (e.g., ductal adenocarcinoma, signet ring cell carcinomas, hepatoid carcinomas, colloid carcinomas, undifferentiated carcinomas, and undifferentiated carcinomas with osteoclast-like giant cells), pancreatic cystic neoplasms (e.g., mucinous cystadenoma, serous cystadenoma, and mucinous ductal ectasia), pancreatic neuroendocrine tumors (e.g., insulinoma, glucagonoma, gastrinoma, VIPoma, and somatostatinoma), papillary cystic neoplasms of the pancreas, lymphoma of the pancreas, and acinar cell tumors of the pancreas, or any described herein.

In another aspect, the invention features a method for the treatment of pain in a subject in need thereof. This method includes administering to the subject an effective amount of any of the foregoing compounds or pharmaceutical compositions.

In another aspect, the invention features a method for the treatment of a respiratory disease (e.g., obstructive lung disease such as, chronic obstructive pulmonary disease) in a subject in need thereof. This method includes administering to the subject an effective amount of any of the foregoing compounds or pharmaceutical compositions.

In another aspect, the invention features a method for the treatment of inflammation (e.g., inflammation related to rheumatoid arthritis, Sjogren's syndrome, coronary artery disease, peripheral vascular disease, hypertension, Alzheimer's disease and its variants, lupus erythematosus, chronic bronchitis, chronic sinusitis, benign prostatichypertrophy) in a subject in need thereof. This method includes administering to the subject an effective amount of any of the foregoing compounds or pharmaceutical compositions.

In another aspect, the invention features a method for the treatment of diabetes in a subject in need thereof. This method includes administering to the subject an effective amount of any of the foregoing compounds or pharmaceutical compositions.

In some embodiments of any of the foregoing methods, the subject is a smoker.

In other embodiments of any of the foregoing methods, the subject is obese.

In another aspect, the invention features a method of increasing the levels of epoxyeicosatrienoic acids in a subject. This method includes administering to the subject an effective amount of any of the foregoing compounds or pharmaceutical compositions.

In another aspect, the invention features a method of decreasing the levels of dihydroxyeicosatrienoic acids in a subject. This method includes administering to the subject an effective amount of any of the foregoing compounds or pharmaceutical compositions.

In another aspect, the invention features a method for the inhibition of soluble epoxide hydrolase in a cell. This method includes contacting a cell with an effective amount of any of the foregoing compounds or pharmaceutical compositions.

In another aspect, the invention features a method of increasing the levels of epoxyeicosatrienoic acids in a cell. This method includes contacting the cell with an effective amount of any of the foregoing compounds or pharmaceutical compositions.

In another aspect, the invention features a method of decreasing the levels of dihydroxyeicosatrienoic acids in a subject. This method includes contacting the cell with an effective amount of any of the foregoing compounds or pharmaceutical compositions.

Chemical Terms

It is to be understood that the terminology employed herein is for the purpose of describing particular embodiments and is not intended to be limiting.

The term "acyl," as used herein, represents a hydrogen or an alkyl group, as defined herein, that is attached to a parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 6, from 1 to 11, or from 1 to 21 carbons.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, or 1 to 6 carbon atoms). An alkylene is a divalent alkyl group.

The term "alkenyl," as used herein, alone or in combination with other groups, refers to a straight-chain or branched hydrocarbon residue having a carbon-carbon double bond and having 2 to 20 carbon atoms (e.g., 2 to 16 carbon atoms, 2 to 10 carbon atoms, 2 to 6, or 2 carbon atoms).

The term "alkynyl," as used herein, alone or in combination with other groups, refers to a straight-chain or branched hydrocarbon residue having a carbon-carbon triple bond and having 2 to 20 carbon atoms (e.g., 2 to 16 carbon atoms, 2 to 10 carbon atoms, 2 to 6, or 2 carbon atoms).

The term "amino," as used herein, represents $-N(R^{N1})_2$, wherein each $R^{N1}$ is, independently, H, OH, $NO_2$, $N(R^{N2})_2$, $SO_2OR^{N2}$, $SO_2R^{N2}$, $SOR^{N2}$, an N-protecting group, alkyl, alkoxy, aryl, arylalkyl, cycloalkyl, acyl (e.g., acetyl, trifluoroacetyl, or others described herein), wherein each of these recited $R^{N1}$ groups can be optionally substituted; or two $R^{N1}$ combine to form an alkylene or heteroalkylene, and wherein each $R^{N2}$ is, independently, H, alkyl, or aryl. The amino groups of the invention can be an unsubstituted amino (i.e., $-NH_2$) or a substituted amino (i.e., $-N(R^{N1})_2$).

The term "aryl," as used herein, refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthyl, 1,2-dihydronaphthyl, indanyl, and 1H-indenyl.

The term "arylalkyl," as used herein, represents an alkyl group substituted with an aryl group. Exemplary unsubstituted arylalkyl groups are from 7 to 30 carbons (e.g., from 7 to 16 or from 7 to 20 carbons, such as $C_{1-6}$ alkyl $C_{6-10}$ aryl, $C_{1-10}$ alkyl $C_{6-10}$ aryl, or $C_{1-20}$ alkyl $C_{6-10}$ aryl), such as, benzyl and phenethyl. In some embodiments, the akyl and the aryl each can be further substituted with 1, 2, 3, or 4 substituent groups as defined herein for the respective groups.

The term "azido," as used herein, represents a $-N_3$ group.

The term "cyano," as used herein, represents a $-CN$ group.

The terms "carbocyclyl," as used herein, refer to a non-aromatic $C_{3-12}$ monocyclic, bicyclic, or tricyclic structure in which the rings are formed by carbon atoms. Carbocyclyl structures include cycloalkyl groups and unsaturated carbocyclyl radicals.

The term "cycloalkyl," as used herein, refers to a saturated, non-aromatic, monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbornyl, and adamantyl.

The term "halogen," as used herein, means a fluorine (fluoro), chlorine (chloro), bromine (bromo), or iodine (iodo) radical.

The term "heteroalkyl," as used herein, refers to an alkyl group, as defined herein, in which one or more of the constituent carbon atoms have been replaced by nitrogen, oxygen, or sulfur. In some embodiments, the heteroalkyl group can be further substituted with 1, 2, 3, or 4 substituent groups as described herein for alkyl groups. Examples of heteroalkyl groups are an "alkoxy" which, as used herein, refers alkyl-O— (e.g., methoxy and ethoxy). A heteroalkylene is a divalent heteroalkyl group.

The term "heteroalkenyl," as used herein, refers to an alkenyl group, as defined herein, in which one or more of the constituent carbon atoms have been replaced by nitrogen, oxygen, or sulfur. In some embodiments, the heteroalkenyl group can be further substituted with 1, 2, 3, or 4 substituent groups as described herein for alkenyl groups. Examples of heteroalkenyl groups are an "alkenoxy" which, as used herein, refers alkenyl-O—. A heteroalkenylene is a divalent heteroalkenyl group.

The term "heteroalkynyl," as used herein, refers to an alkynyl group, as defined herein, in which one or more of the constituent carbon atoms have been replaced by nitrogen, oxygen, or sulfur. In some embodiments, the heteroalkynyl group can be further substituted with 1, 2, 3, or 4 substituent groups as described herein for alkynyl groups. Examples of heteroalkynyl groups are an "alkynoxy" which, as used herein, refers alkynyl-O—. A heteroalkynylene is a divalent heteroalkynyl group.

The term "heteroaryl," as used herein, refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group. Examples of heteroaryl groups are pyridyl, pyrazoyl, benzooxazolyl, benzoimidazolyl, benzothiazolyl, imidazolyl, oxaxolyl, and thiazolyl.

The term "heteroarylalkyl," as used herein, represents an alkyl group substituted with a heteroaryl group. Exemplary unsubstituted heteroarylalkyl groups are from 7 to 30 carbons (e.g., from 7 to 16 or from 7 to 20 carbons, such as $C_{1-6}$ alkyl $C_{2-9}$ heteroaryl, $C_{1-10}$ alkyl $C_{2-9}$ heteroaryl, or $C_{1-20}$ alkyl $C_{2-9}$ heteroaryl). In some embodiments, the akyl and the heteroaryl each can be further substituted with 1, 2, 3, or 4 substituent groups as defined herein for the respective groups.

The term "heterocyclyl," as used herein, denotes a mono- or polycyclic radical having 3 to 12 atoms having at least one ring containing one, two, three, or four ring heteroatoms selected from N, O or S, wherein no ring is aromatic. Examples of heterocyclyl groups include, but are not limited to, morpholinyl, thiomorpholinyl, furyl, piperazinyl, piperidinyl, pyranyl, pyrrolidinyl, tetrahydropyranyl, tetrahydrofuranyl, and 1,3-dioxanyl.

The term "heterocyclylalkyl," as used herein, represents an alkyl group substituted with a heterocyclyl group. Exemplary unsubstituted heterocyclylalkyl groups are from 7 to 30 carbons (e.g., from 7 to 16 or from 7 to 20 carbons, such as $C_{1-6}$ alkyl $C_{2-9}$ heterocyclyl, $C_{1-10}$ alkyl $C_{2-9}$ heterocyclyl, or $C_{1-20}$ alkyl $C_{2-9}$ heterocyclyl). In some embodiments, the akyl and the heterocyclyl each can be further substituted with 1, 2, 3, or 4 substituent groups as defined herein for the respective groups.

The term "hydroxyl," as used herein, represents an —OH group.

The term "N-protecting group," as used herein, represents those groups intended to protect an amino group against undesirable reactions during synthetic procedures. Commonly used N-protecting groups are disclosed in Greene, "Protective Groups in Organic Synthesis," $3^{rd}$ Edition (John Wiley & Sons, New York, 1999). N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, and phenylalanine; sulfonyl-containing groups such as benzenesulfonyl, and p-toluene-sulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, arylalkyl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —NO₂ group.

The term "thiol," as used herein, represents an —SH group.

The alkyl, alkenyl, alkynyl, heteroalkyl, heteroalkenyl, heteroalkynyl, carbocyclyl (e.g., cycloalkyl), aryl, heteroaryl, and heterocyclyl groups may be substituted or unsubstituted. When substituted, there will generally be 1 to 4 substituents present, unless otherwise specified. Substituents include, for example: aryl (e.g., substituted and unsubstituted phenyl), carbocyclyl (e.g., substituted and unsubstituted cycloalkyl), halogen (e.g., fluoro), hydroxyl, heteroalkyl (e.g., substituted and unsubstituted methoxy, ethoxy, or thioalkoxy), heteroaryl, heterocyclyl, amino (e.g., NH₂ or mono- or dialkyl amino), azido, cyano, nitro, or thiol. Aryl, carbocyclyl (e.g., cycloalkyl), heteroaryl, and heterocyclyl groups may also be substituted with alkyl (unsubstituted and substituted such as arylalkyl (e.g., substituted and unsubstituted benzyl)).

Compounds of the invention can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. "Racemate" or "racemic mixture" means a compound containing two enantiomers, wherein such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99% or 99.9%) by weight relative to the other stereoisomers. When a single enantiomer is named or depicted by structure, the depicted or named enantiomer is at least 60%, 70%, 80%, 90%, 99% or 99.9% by weight optically pure. When a single diastereomer is named or depicted by structure, the depicted or named diastereomer is at least 60%, 70%, 80%, 90%, 99% or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99% or 99.9% by mole fraction pure relative to the other stereoisomers. When a single enantiomer is named or depicted by structure, the depicted or named enantiomer is at least 60%, 70%, 80%, 90%, 99% or 99.9% by mole fraction pure. When a single diastereomer is named or depicted by structure, the depicted or named diastereomer is at least 60%, 70%, 80%, 90%, 99% or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s) or mixtures of diastereomers in which one or more diastereomer is enriched relative to the other diastereomers. The invention embraces all of these forms.

Definitions

In the practice of the methods of the present invention, an "effective amount" of any one of the compounds of the invention or a combination of any of the compounds of the invention or a pharmaceutically acceptable salt thereof, is administered via any of the usual and acceptable methods known in the art, either singly or in combination.

The term "epoxyeicosatrienoic acid," as used herein, refers to signaling molecules formed by the action of cytochrome P450 epoxygenase on 20-carbon essential fatty acids, such as arachidonic acid. "Dihydroxyeicosatrienoic acids" are the corresponding vicinal diols that result from hydrolysis of an epoxyeicosatrienoic acid, e.g., by soluble epoxide hydrolase. The term "increasing the levels of epoxyeicosatrienoic acids," as used herein, refers to an increase of the total level of epoxyeicosatrienoic acids in a subject after administration of a compound of the invention compared to the total level of epoxyeicosatrienoic acids in a subject prior to administration. The term "decreasing the levels of dihydroxyeicosatrienoic acids," as used herein, refers to an increase of the total level of dihydroxyeicosatrienoic acids in a subject after administration of a compound of the invention compared to the total level of dihydroxyeicosatrienoic acids in a subject prior to administration.

The term "inhibition of soluble epoxide hydrolase," as used herein, refers to inhibition of the enzyme activity of soluble epoxide hydrolase with an $IC_{50}$ of less than 10 μM (e.g., less than 5 μM, less than 1 μM, less than 500 nM, less than 100 nM, less than 10 nM). The enzymatic activity of soluble epoxide hydrolase may be determined using any method known in the art, for example, activity may be determined with an assay that utilizes (3-phenyl-oxiranyl)-acetic acid cyano-(6-methoxy-naphthalen-2-yl)-methyl ester (PHOME) as a substrate. In this particular assay, hydrolysis of PHOME by epoxide hydrolase produces the highly fluorescent 6-methoxy-2-naphthaldehyde which can be analyzed using an excitation wavelength of 330 nm and emission wavelength of 465 nm.

The term "pharmaceutical composition," as used herein, represents a composition containing a compound described herein formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

A "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

As used herein, the term "pharmaceutically acceptable salt" means any pharmaceutically acceptable salt of the compound of formula (I). For example pharmaceutically acceptable salts of any of the compounds described herein include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. H. Stahl and C. G. Wermuth), Wiley-VCH, 2008. The salts can be prepared in situ during the final isolation and purification of the compounds described herein or separately by reacting a free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palm itate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

As used herein, the term "subject" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the terms "treat," "treated," or "treating" mean both therapeutic treatment and prophylactic or preventative measures wherein the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

DETAILED DESCRIPTION OF THE INVENTION

Compounds

The invention features compounds capable of inhibiting the activity of soluble epoxide hydrolase. Exemplary compounds described herein include compounds having a structure according to formula I:

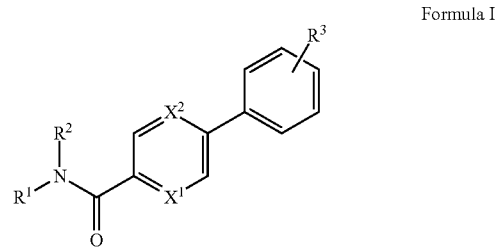

Formula I or pharmaceutically acceptable salts thereof.

In some embodiments, the compound has the structure:

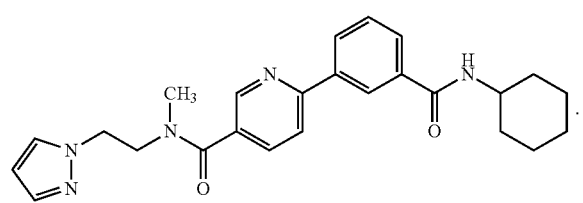

1

Other embodiments, as well as exemplary methods for the synthesis or production of these compounds, are described herein.

Pharmaceutical Uses

The compounds described herein are useful in the methods of the invention and, while not bound by theory, are believed to exert their desirable effects through their ability to inhibit the activity of soluble epoxide hydrolase.

Soluble epoxide hydrolase (sEH) is a bifunctional enzyme that in humans is encoded by the EPHX2 gene, mutations of which have been associated with familial hypercholesterolemia. sEH is a member of the epoxide hydrolase family, and is found in both the cytosol and peroxisomes. sEH binds to specific epoxides and converts them to the corresponding diols. sEH also has lipid-phosphate phosphatase activity. sEH is highly expressed in the liver, and is also expressed in the vascular endothelium, leukocytes, red blood cells, smooth muscle cells, adipocytes, and the kidney proximal tubule.

Through metabolism of epoxyeicosatrienoic acids (EETs) and other lipid mediators, sEH plays a role in several diseases, including respiratory diseases, cardiovascular disease, cancer, pain, and even diabetes. sEH inhibitors have been shown to effectively increase the levels of epoxyeicosatrienoic acids and reduce the levels of dihydroxyeicosatrienoic acids. As epoxyeicosatrienoic acids have been shown to have anti-inflammatory properties, an increase in EET levels may result in therapeutic effects in many diseases, including those described above.

Combination Formulations and Uses Thereof

The compounds of the invention can be combined with one or more therapeutic agents. In particular, the therapeutic agent can be one that treats or prophylactically treats any disorder described herein, such as cardiovascular disease, respiratory disease, cancer, inflammation, pain, or diabetes.

Combination Therapies

A compound of the invention can be used alone or in combination with other agents that have sEH-inhibiting activity, or in combination with other types of treatment (which may or may not inhibit sEH) to treat, prevent, and/or reduce the risk of any disorders that benefit from sEH inhibition. In combination treatments, the dosages of one or more of the therapeutic compounds may be reduced from standard dosages when administered alone. For example, doses may be determined empirically from drug combinations and permutations or may be deduced by isobolographic analysis (e.g., Black et al., *Neurology* 65:S3-S6, 2005). In this case, dosages of the compounds when combined should provide a therapeutic effect.

Pharmaceutical Compositions

The compounds of the invention are preferably formulated into pharmaceutical compositions for administration to human subjects in a biologically compatible form suitable for administration in vivo. Accordingly, in another aspect, the present invention provides a pharmaceutical composition comprising a compound of the invention in admixture with a suitable diluent, carrier, or excipient.

The compounds of the invention may be used in the form of the free base, in the form of salts, solvates, and as prodrugs. All forms are within the scope of the invention. In accordance with the methods of the invention, the described compounds or salts, solvates, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, and wafers.

A compound of the invention may also be administered parenterally. Solutions of a compound of the invention can be prepared in water suitably mixed with a surfactant, such as hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003, 20$^{th}$ ed.) and in The United States Pharmacopeia: The National Formulary (USP 24 NF19), published in 1999.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe.

Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer.

Compositions suitable for buccal or sublingual administration include tablets, lozenges, and pastilles, where the active ingredient is formulated with a carrier, such as sugar, acacia, tragacanth, gelatin, and glycerine. Compositions for rectal administration are conveniently in the form of suppositories containing a conventional suppository base, such as cocoa butter.

The compounds of the invention may be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

Dosages

The dosage of the compounds of the invention, and/or compositions comprising a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, satisfactory results may be obtained when the compounds of the invention are administered to a human at a daily dosage of, for example, between 0.05 mg and 3000 mg (measured as the solid form). Dose ranges include, for example, between 10-1000 mg (e.g., 50-800 mg). In some embodiments, 50, 100, 150, 200, 250, 300, 350, 400, 450, 500, 550, 600, 650, 700, 750, 800, 850, 900, 950, or 1000 mg of the compound is administered. Preferred dose ranges include, for example, between 0.05-15 mg/kg or between 0.5-15 mg/kg.

Alternatively, the dosage amount can be calculated using the body weight of the patient. For example, the dose of a compound, or pharmaceutical composition thereof, administered to a patient may range from 0.1-50 mg/kg (e.g., 0.25-25 mg/kg). In exemplary, non-limiting embodiments, the dose may range from 0.5-5.0 mg/kg (e.g., 0.5, 1.0, 1.5, 2.0, 2.5, 3.0, 3.5, 4.0, 4.5, or 5.0 mg/kg) or from 5.0-20 mg/kg (e.g., 5.5, 6.0, 6.5, 7.0, 7.5, 8.0, 8.5, 9.0, 9.5, 10, 11, 12, 13, 14, 15, 16, 17, 18, 19, or 20 mg/kg).

EXAMPLES

Example 1. General Synthesis

Compounds of the invention may be synthesized as shown in Scheme 1.

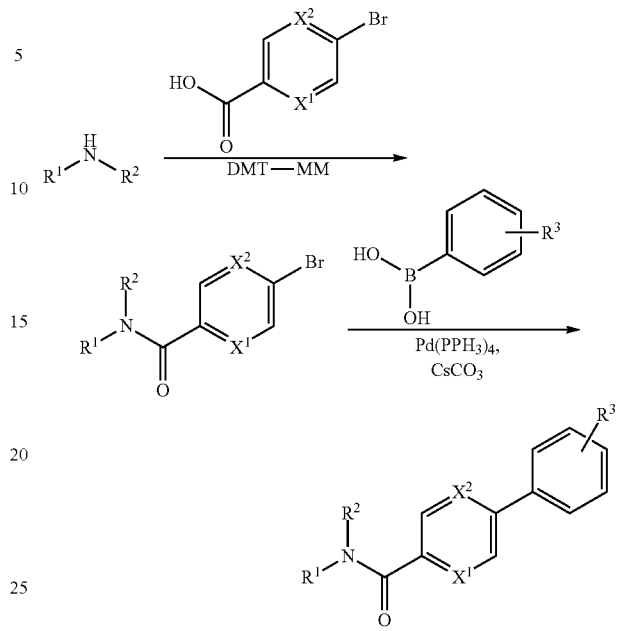

Scheme 1. General Synthesis of Compounds of the Invention

Acylation of amines with bromoarylcarboxylates provide bromoarylcarbamides. Subsequent Suzuki cross-coupling with aryl boronic acids or esters results in compounds of formula I.

Example 2. Synthesis of Compound 1

Compound 1 was synthesized as shown in Scheme 2.

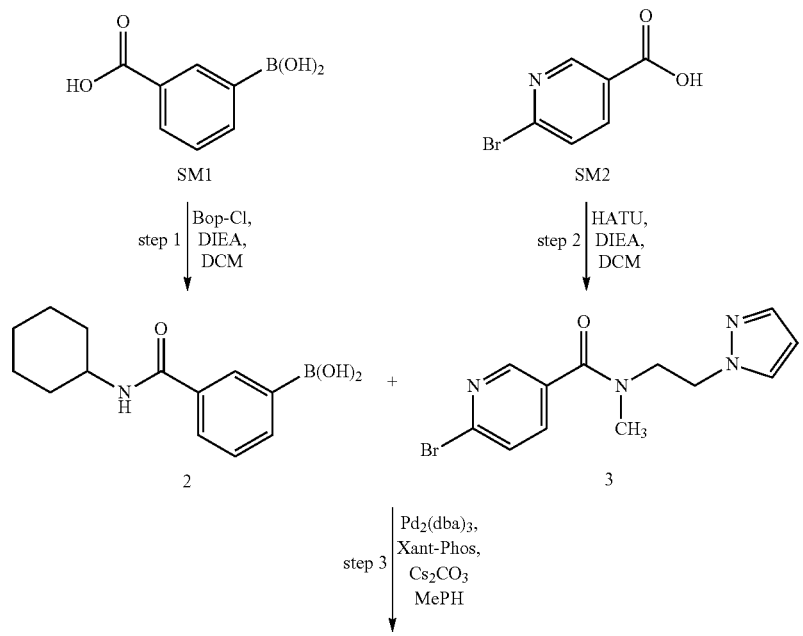

Scheme 2. Synthesis of Compound 1

-continued

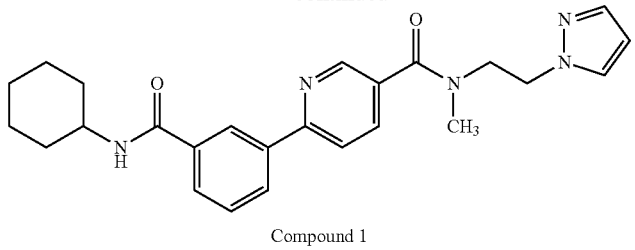

Compound 1

Step 1: Synthesis of 3-(cyclohexylcarbamoyl)phenylboronic Acid (Compound 2)

To a solution of SM1 (166 mg, 1 mmol) in dichloromethane (10 mL) was added bis(2-oxo-3-oxazolidinyl)phosphinic chloride (305 mg, 1.2 mmol) and diisopropylethylamine (310 mg, 2.4 mmol) at room temperature. After stirring for 0.5 hour, cyclohexanamine (99 mg, 1 mmol) was added. The reaction mixture was stirred at room temperature for 4 hours. The resulting solution was diluted with dichloromethane (20 mL), washed with 10% citric acid solution (2×15 mL), a saturated sodium bicarbonate solution (2×15 mL), brine (20 mL), dried over sodium sulfate, and filtered. The solvent was removed under reduced pressure to afford the crude product (207 mg, 83.8%) as a white solid. LC-MS (M+H)$^+$=248.

Step 2: Synthesis of N-(2-(1H-pyrazol-1-yl)ethyl)-6-bromo-N-methylnicotinamide (Compound 3)

To a solution of SM2 (201 mg, 1 mmol) in dichloromethane (10 mL) was added 1-[bis(dimethylamino)methylene]-1H-1,2,3-triazolo[4,5-]pyridinium 3-oxide hexafluorophosphate (456 mg, 1.2 mmol) and diisopropylethylamine (310 mg, 2.4 mmol) at room temperature. After stirring for 0.5 hour, N-methyl-2-(1H-pyrazol-1-yl)ethanamine (125 mg, 1 mmol) was added. The reaction mixture was stirred at room temperature for 2 hours. The resulting solution was diluted with dichloromethane (20 mL), washed with 10% citric acid solution (2×15 mL), a saturated sodium bicarbonate solution (2×15 mL), brine (20 mL), dried over sodium sulfate, and filtered. The solvent was removed under reduced pressure to afford the crude product (215 mg, 70%) as a yellow solid. LC-MS (M+H)$^+$=309.

Step 3: Synthesis of N-(2-(1H-pyrazol-1-yl)ethyl)-6-(3-(cyclohexylcarbamoyl)phenyl)-N-methylnicotinamide (Compound 1)

A mixture of Compound 2 (207 mg, 0.84 mmol), Compound 3 (215 mg, 0.7 mmol), Pd$_2$(dba)$_2$ (176 mg, 0.168 mmol), Xant-Phos (97 mg, 0.168 mmol) and cesium carbonate (1.5 g, 14.1 mmol) in toluene (20 ml) was stirred at 90° C. under nitrogen overnight. The resulting solution was diluted with ethyl acetate (40 mL) and filtered, the filtrate was concentrated under reduced pressure, and purified by prep-HPLC to give Compound 1 (150 mg, 50%) as a white solid. LC-MS (M+H)$^+$=432. $^1$H NMR (300 MHz, DMSO) δ 8.57 (s, 1H), 8.51 (s, 1H), 8.22 (d, 1H), 8.05 (s, 1H), 8.03 (d, 1H), 7.93 (d, 1H), 7.74 (s, 1H), 7.72 (s, 1H), 7.59 (t, 1H), 7.47 (s, 1H), 6.27 (s, 1H), 4.39 (t, 2H), 3.83 (m, 3H), 2.88 (s, 3H), 1.89-1.63 (m, 5H), 1.41-1.30 (m, 4H), 1.25-1.16 (m, 1H).

Example 3. sEH Inhibition Assay

Protocol

The sEH inhibition assay was conducted in costar 384 well black NBS plates (Corning). The assay buffer used was 25 mM Tris pH 7.0 and 0.1 mg/ml BSA. The enzyme was purchased from Cayman Chemical (10011669) at a stock concentration of 15.625 μM. The Epoxy Fluor 7 substrate also from Cayman Chemical (10008610) was dissolved in DMSO at a concentration of 25.68 mM. This was further diluted ten-fold in DMSO to a concentration of 2.568 mM. Competition assays were performed with 5 μL Epoxy Fluor 7 diluted from DMSO stock to a final concentration of 5 nM, 5 μL of competitor (final concentration 10 μM-0.5 nM), and 10 μL enzyme (final concentration of 3 nM) in the assay buffer for a total volume of 20 μL. The compound was pre-incubated with enzyme for 15 min at room temperature prior to addition of substrate. The plate was read kinetically at excitation 330 nm and emission 465 nm wavelengths at 30° C. for 20 minutes on the Tecan M1000. The rate was calculated for the linear portion of the curves (2.5-12.5 minutes) and data fit to a sigmoidal curve.

Results

By following the above protocol, Compound 1 was found to have an IC$_{50}$ of 2 nM against sEH.

Other Embodiments

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

Other embodiments are in the claims.

What is claimed is:

1. A compound having the structure:

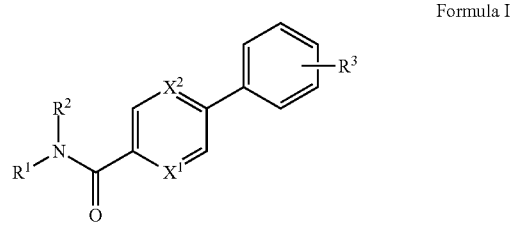

Formula I wherein one of X$^1$ or X$^2$ is N and the other is CH;
R$^1$ is hydrogen, C$_1$-C$_6$ acyl, C$_1$-C$_6$ alkyl, C$_2$-C$_6$ alkenyl, C$_2$-C$_6$ alkynyl, C$_1$-C$_6$ heteroalkyl, C$_2$-C$_6$ heteroalkenyl, $C_2$-$C_6$ heteroalkynyl, $C_3$-$C_{10}$ carbocyclyl, $C_6$-$C_{10}$ aryl, $C_6$-$C_{10}$ aryl $C_1$-$C_6$ alkyl, $C_2$-$C_9$ heterocyclyl, or $C_2$-$C_9$ heterocyclyl $C_1$-$C_6$ alkyl;

$R^2$ is hydrogen or $C_1$-$C_6$ alkyl;

$R^3$ is C(O)NHR$^4$; and $R^4$ is hydrogen, $C_1$-$C_6$ acyl, $C_1$-$C_6$ alkyl, $C_2$-$C_6$ alkenyl, $C_2$-$C_6$ alkynyl, $C_1$-$C_6$ heteroalkyl, $C_2$-$C_6$ heteroalkenyl, $C_2$-$C_6$ heteroalkynyl, $C_3$-$C_{10}$ carbocyclyl, $C_6$-$C_{10}$ aryl, $C_6$-$C_{10}$ aryl $C_1$-$C_6$ alkyl, $C_2$-$C_9$ heterocyclyl, $C_2$-$C_9$ heterocyclyl $C_1$-$C_6$ alkyl;

or a pharmaceutically acceptable salt thereof.

2. The compound of claim 1, wherein said compound has the structure:

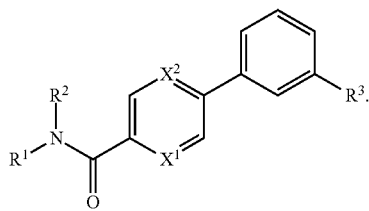

3. The compound of claim 1, wherein $R^4$ is $C_3$-$C_{10}$ carbocyclyl or $C_6$-$C_{10}$ aryl $C_1$-$C_6$ alkyl.

4. The compound of claim 3, wherein $R^4$ is $C_3$-$C_{10}$ carbocyclyl.

5. The compound of claim 4, wherein said $C_3$-$C_{10}$ carbocyclyl is cyclohexyl.

6. The compound of claim 3, wherein $R^4$ is $C_6$-$C_{10}$ aryl $C_1$-$C_6$ alkyl.

7. The compound of claim 6, wherein said $C_6$-$C_{10}$ aryl $C_1$-$C_6$ alkyl is benzyl.

8. The compound of claim 1, wherein $R^2$ is $C_1$-$C_6$ alkyl.

9. The compound of claim 8, wherein said $C_1$-$C_6$ alkyl is methyl.

10. The compound of claim 1, wherein $X^1$ is N and $X^2$ is CH.

11. The compound of claim 1, wherein $X^1$ is CH and $X^2$ is N.

12. The compound of claim 1, wherein $R^1$ is $C_2$-$C_9$ heterocyclyl $C_1$-$C_6$ alkyl.

13. A compound having the structure:

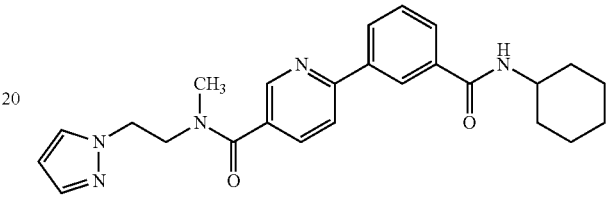

or a pharmaceutically acceptable salt thereof.

14. A pharmaceutical composition comprising the compound of claim 1 and a pharmaceutically acceptable excipient.

* * * * *